United States Patent
Nicolau et al.

[11] Patent Number: 5,948,724
[45] Date of Patent: Sep. 7, 1999

[54] VINYL ACETATE CATALYST COMPRISING METALLIC PALLADIUM AND GOLD AND CUPRIC ACETATE

[75] Inventors: Ioan Nicolau; Jerry A. Broussard; Philip M. Colling, all of Corpus Christi, Tex.

[73] Assignee: Celanese International Corporation, Dallas, Tex.

[21] Appl. No.: 08/959,897

[22] Filed: Oct. 29, 1997

[51] Int. Cl.[6] .................. B01J 23/72; B01J 23/44
[52] U.S. Cl. .................. 502/331; 502/325; 502/330; 502/333
[58] Field of Search .................. 502/325, 330, 502/331, 333

[56] References Cited

U.S. PATENT DOCUMENTS

| | | |
|---|---|---|
| 3,775,342 | 11/1973 | Kronig et al. . |
| 3,822,308 | 7/1974 | Kronig et al. . |
| 4,093,559 | 6/1978 | Fernholz et al. .................. 502/170 |
| 4,119,567 | 10/1978 | Bartsch .................. 502/170 |
| 4,199,436 | 4/1980 | Courty .................. 208/62 |
| 4,201,661 | 5/1980 | Jujuin et al. .................. 208/138 |
| 4,698,324 | 10/1987 | Haruta et al. .................. 502/243 |
| 5,208,203 | 5/1993 | Horiuchi et al. .................. 502/302 |
| 5,332,710 | 7/1994 | Nicolau et al. .................. 502/243 |
| 5,347,046 | 9/1994 | White et al. .................. 560/245 |
| 5,627,125 | 5/1997 | Ebner et al. .................. 502/331 |
| 5,693,586 | 12/1997 | Nicolau et al. .................. 502/330 |

FOREIGN PATENT DOCUMENTS

WO94/08714  4/1994  WIPO .

*Primary Examiner*—Elizabeth D Wood
*Attorney, Agent, or Firm*—M. Susan Spiering

[57] ABSTRACT

A catalyst for the production of vinyl acetate by reaction of ethylene, oxygen and acetic acid comprising a porous support on the porous surfaces of which is deposited catalytically effective amounts of metallic palladium and gold, and cupric acetate. Use of this catalyst results in a reaction having a relatively low selectivity to carbon dioxide.

7 Claims, No Drawings

VINYL ACETATE CATALYST COMPRISING METALLIC PALLADIUM AND GOLD AND CUPRIC ACETATE

BACKGROUND OF THE INVENTION

1. Field of the Invention

This invention relates to new and improved catalysts for the production of vinyl acetate by reaction of ethylene, oxygen and acetic acid.

2. Background Information Including Description of Related Art

It is known to produce vinyl acetate by reaction of ethylene, oxygen and acetic acid using a catalyst consisting of metallic palladium and gold supported on a carrier. While the process utilizing such a catalyst is capable of producing vinyl acetate at fair levels of productivity, such productivity levels are limited by the production of undesirable by-products, particularly carbon dioxide. The production of any product or by-product can be expressed as percent selectivity, defined as the amount of such product expressed as a percentage of the theoretical maximum which could be produced from the reactants. Thus, any expedient which results in a reduced production of carbon dioxide expressed as lower percent $CO_2$ selectivity, is very desirable.

The following references may be considered material to the invention claimed herein.

U.S. Pat. Nos. 3,775,342 issued Nov. 27, 1973, and 3,822,308 issued Jul. 2, 1974, both to Kronig et al., each discloses a method of making vinyl acetate catalysts comprising treating a support simultaneously or successively with a solution A containing dissolved salts of noble metals such as palladium and gold, and a solution B containing compounds able to react on the support with the noble metal salts to form water insoluble compounds of the metals, treating such water-insoluble compounds with a reducing agent to convert the water-insoluble noble metal compounds to the metals, washing the catalyst to remove water-soluble compounds, and applying an alkali metal compound e.g. an alkali metal carboxylate before or after treatment with the reducing agent. Solution A can optionally also contain salts of any of several other metals, including copper.

U.S. Pat. No. 5,332,710, issued Jul. 26, 1994, to Nicolau et al., discloses a method of preparing a catalyst useful for the production of vinyl acetate by reaction of ethylene, oxygen and acetic acid, comprising impregnating a porous support with water soluble salts of palladium and gold, fixing the palladium and gold as insoluble compounds on the support by immersing and tumbling the impregnated support in a reactive solution to precipitate such compounds, and subsequently reducing the compounds to their metallic form.

U.S. Pat. No. 5,347,046, issued Sep. 13, 1994, to White et al., discloses catalysts for the production of vinyl acetate by reaction of ethylene, oxygen, and acetic acid, comprising a palladium group metal and/or a compound thereof, gold and/or a compound thereof, and copper, nickel, cobalt, iron, manganese, lead or silver, or a compound thereof, preferably deposited on a support material.

SUMMARY OF THE INVENTION

In accordance with this invention, a catalyst is provided useful for the production of vinyl acetate by reaction of ethylene, oxygen and acetic acid with low carbon dioxide selectivity, comprising a porous support on the porous surfaces of which are deposited catalytically effective amounts of metallic palladium and gold, and cupric acetate.

The copper in the cupric acetate is believed to effect a lower carbon dioxide selectivity, which is often accompanied by a higher vinyl acetate productivity, than when no cupric acetate is present in the catalyst.

DETAILED DESCRIPTION OF THE INVENTION

The support material in the catalyst of this invention is composed of particles having any of various regular or irregular shapes, such as spheres, tablets, cylinders, rings, stars, or other shapes, and may have dimensions such as diameter, length or width of about 1 to about 10 mm, preferably about 3 to 9 mm. Spheres having a diameter of about 4 to about 8 mm are preferred. The support material may be composed of any suitable porous substance, e.g., silica, alumina, silica-alumina, titania, zirconia, silicates, aluminosilicates, titanates, spinel, silicon carbide, carbon, and the like.

The support material may have a surface area within the range, for example, of about 10 to about 350, preferably about 100 to about 200 $m^2/g$, an average pore size in the range, for example, of about 50 to about 2000 angstroms, and a pore volume in the range, for example, of about 0.1 to 2, preferably about 0.4 to about 1.2 ml/g.

In the preparation of the catalyst used in the process of this invention, the support material is first treated to deposit catalytic amounts of palladium and gold on the porous surfaces of the support particles. Any of various methods for accomplishing this purpose may be used, all of which involve simultaneous or separate impregnations of the support with one or more aqueous solutions of water-soluble compounds of palladium and/or gold. Palladium (II) chloride, sodium palladium (II) chloride, potassium palladium (II) chloride, palladium (II)nitrate or palladium (II) sulfate are examples of suitable water-soluble palladium compounds, while an alkali metal, e.g., sodium or potassium salt of auric (III) chloride or tetrachloroauric (III) acid can be used as the water-soluble gold compound. An alkali metal salt of tetrachloroauric (III) acid, and sodium palladium (II) chloride are preferred salts for impregnation because of their good water solubility. The impregnation can be accomplished by the "incipient wetness" method wherein an amount of water-soluble metal compound solution used for the impregnation is from about 95 to about 100 percent of the absorptive capacity of the support material. The concentration of the solution or solutions is such that the amount of elemental palladium and gold in the solution or solutions absorbed on the support is equal to a desired predetermined amount. If more than one such impregnation is carried out, then each impregnation may contain water-soluble compound equivalent to all or only a portion of the amount of one or any combination of the two catalytically active metals desired in the final catalyst, as long as the amounts of such metals in the total of the impregnating solutions absorbed are equal to the final desired amounts. In particular, it may be desirable to impregnate the support with more than one solution of a water-soluble gold compound, as more fully described hereinafter. The impregnations are such as to provide, for example, about 1 to about 10 grams of elemental palladium and, for example, about 0.5 to about 10 grams of elemental gold, with the amount of gold being from about 10 to about 125 wt. % based on the weight of palladium.

After each impregnation of the support with an aqueous solution of water-soluble salt of palladium and/or gold, the metal is "fixed", i.e., precipitated, as a water-insoluble compound such as the hydroxide, by reaction with an appropriate alkaline compound, e.g., an alkali metal hydroxide, silicate, borate, carbonate or bicarbonate, in aqueous solution. Sodium and potassium hydroxides are preferred alkaline fixing compounds. The alkali metal in the alkaline compound should be in an amount of, for example, about 1 to about 2, preferably about 1.1 to about 1.8 times the amount necessary to react with the catalytically active cations present in the watersoluble salt. The fixing of the metal may be done by the incipient wetness method wherein the impregnated support is dried, e.g., at a temperature of 150° C. for one hour, contacted with an amount of solution of the alkaline material equal to about 95–100% of the pore volume of the support, and allowed to stand for a period of about ½ to about 16 hours; or the roto-immersion method wherein the impregnated support without drying is immersed in a solution of the alkaline material and is rotated and/or tumbled during at least the initial period of precipitation such that a thin band of the precipitated water-soluble compound is formed at or near the surface of the support particles. The rotation and tumbling may be cared out, for example, at about 1 to about 10 rpm for a period e.g., of at least about 0.5 hour, preferably about 0.5 to about 4 hours. The contemplated roto-immersion method is disclosed in U.S. Pat. No. 5,332,710, the entire disclosure of which is incorporated herein by reference.

The fixed, i.e., precipitated palladium and gold compounds may then be reduced, for example, in the vapor phase with ethylene, e.g., 5% in nitrogen at 150° C. for 5 hours, after first washing the catalyst containing the fixed metal compounds until it is free of anions such as halide, and drying, e.g., at 150° C. for about 1 hour, or such reduction may be accomplished before washing and drying in the liquid phase at room temperature with an aqueous solution of hydrazine hydrate wherein the excess of hydrazine over that required to reduce all the metal compounds present on the support is in the range, for example, of about 8:1 to about 15:1, followed by washing and drying. Other reducing agents and means for reducing the fixed metal compounds present on the support may be employed as conventional in the art. The reduction of the fixed metal compound mainly results in the formation of the metal, although a minor amount of metal oxide may also be present. In preparations using more than one impregnation and fixing steps, the reduction may be carried out after each fixing step or after the total of the metallic elements have been fixed on the support.

As an example of foregoing general procedure, a "separate fix" method may be used to fix the catalytically active metallic elements on the support and reduce the water-insoluble metal compounds to the desirable metallic form prior to the impregnation with cupric acetate. In this method, using the specific procedures described previously, the support is first impregnated with an aqueous solution of a water-soluble compound of palladium by incipient wetness, and the palladium is then fixed by treatment with an alkaline fixing solution by incipient wetness or roto-immersion, preferably roto-immersion. The catalyst is then dried and separately impregnated with a solution of a soluble gold compound having the amount of elemental gold desired in the catalyst, and the gold is fixed by treatment with an alkaline fixing solution by incipient wetness or roto-immersion, preferably incipient wetness. If the gold is to be fixed by the incipient wetness method, such fixing may be combined with the impregnation step by using a single aqueous solution of soluble gold compound and alkaline fixing compound in an amount in excess of that necessary to convert all the gold in the solution to a fixed insoluble gold compound, e.g., auric hydroxide. If a hydrocarbon such as ethylene, or hydrogen is to be used in the vapor phase as reducing agent, the catalyst containing the fixed metal compounds is washed until it is free of anions, dried, and reduced with ethylene or other hydrocarbon as previously described. If hydrazine is to be used in the liquid phase as reducing agent, the catalyst containing the fixed metal compounds is treated with an aqueous solution of excess hydrazine hydrate before washing and drying to reduce the metal compounds to the metals, and the catalyst is then washed and dried as described.

Another specific method of preparing the catalyst prior to the impregnation with cupric acetate is a "modified roto-immersion" method in which only part of the gold is impregnated with the palladium in a first impregnation, the metals are fixed by reaction with an alkaline fixing compound by roto-immersion, the fixed metal compounds are reduced to the free metals, e.g., with ethylene or hydrazine hydrate, with washing and drying done before an ethylene reduction or after a hydrazine reduction. The catalyst is then impregnated with the remainder of the gold in the form of a solution of water soluble gold compound, and the catalyst is again reduced, e.g., with ethylene or hydrazine, after or before washing and drying, as described previously. This modified roto-immersion method is more fully described in International Publication No. WO94/08714 dated Apr. 28, 1994, the entire disclosure of which is incorporated herein by reference.

After the catalyst containing palladium and gold in metallic form deposited on a support material is prepared by any of the foregoing methods, it is impregnated with an aqueous solution of cupric acetate, either monohydrate or anhydrous, preferably by incipient wetness. The catalyst is then dried such that the finished catalyst contains cupric acetate in an amount equivalent to, for example, about 0.3 to about 5.0, preferably about 0.5 to about 3.0 grams of elemental copper per liter of finished catalyst.

Advantageously, the catalyst containing palladium and gold in metallic form may also be impregnated with a solution of an alkali metal acetate, preferably potassium or sodium acetate, and most preferably potassium acetate. After drying, the finished catalyst may contain, for example, about 10 to about 70, preferably about 20 to about 60 grams of alkali metal acetate per liter of finished catalyst. The optional impregnation of the catalyst with alkali metal acetate, when carried out, may be accomplished before or after the impregnation with cupric acetate. Preferably, however, the alkali metal acetate impregnation is combined with that of cupric acetate, i.e., the catalyst containing metallic palladium and gold is impregnated with a single solution of both cupric acetate and alkali metal acetate to yield a finished catalyst which after drying contains the desired amounts of both acetates.

When vinyl acetate is prepared using the catalyst of the present invention, a stream of gas, which contains ethylene, oxygen or air, acetic acid, and desirably an alkali metal acetate, is passed over the catalyst. The composition of the gas stream can be varied within wide limits, taking in account explosive limits. For example, the molar ratio of ethylene to oxygen can be about 80:20 to about 98:2, the molar ratio of acetic acid to ethylene can be about be from 100:1 to about 1:100, preferably about 10:1 to about 1:8, and the content of gaseous alkali metal acetate can be about 1 to about 100 ppm based on the weight of acetic acid employed. The gas stream also can contain other inert gases, such as nitrogen, carbon dioxide and/or saturated hydrocarbons. Reaction temperatures which can be used are elevated temperatures, preferably those in the range of about 150–220° C. The pressure employed can be a somewhat reduced pressure, normal pressure or elevated pressure, preferably a pressure of up to about 20 atmospheres gauge.

An advantageous variant of a process for producing vinyl acetate using the catalyst of this invention is the inclusion of a non-halogen containing copper compound in the feed stream of reactants to the process. The non-halogen containing copper compound is preferably somewhat water soluble or acetic acid soluble e.g., at least about 0.3 g/l at 20° C., and may be, for example cupric acetate (anhydrous or monohydrate) which is preferred, cupric nitrate trihydrate or hexahydrate, cupric sulfate (anhydrous or pentahydrate), or cupric formate (anhydrous or pentahydrate) and the like. The amount of the copper compound fed to the reaction can be such as to provide, for example, about 10 ppb (parts per billion) to about 50 ppm (parts per million), preferably about 20 ppb to about 10 ppm of elemental copper relative to acetic acid in the feed stream. By means of this feature, the amount of copper in the cupric acetate of the catalyst lost by the catalyst volatilization during long term use is reduced, resulting in less of a rise in carbon dioxide selectivity.

The following example further illustrates the invention.

EXAMPLE

In this example, the catalyst containing palladium and gold in their metallic state on a support material, is prepared by the "separate fix" method and is subsequently impregnated with cupric acetate and potassium acetate.

A support material consisting of Sud Chemie KA-160 silica spheres having a nominal diameter of 7 mm, a surface area of about 160–175 $m^2/g$, and a pore volume of about 0.68 ml/g, was first impregnated by incipient wetness with an aqueous solution of sodium palladium (II) chloride sufficient to provide about 7 grams of elemental palladium per liter of catalyst. The palladium was then fixed to the support as palladium (II) hydroxide by treating the catalyst by roto-immersion with an aqueous sodium hydroxide solution such that the Na/Cl molar ratio was about 1.2:1. The catalyst was then dried at 100° C. for 1 hour in a fluid bed drier following which it was impregnated by incipient wetness with an aqueous solution of sodium tetrachloroaurate in an amount sufficient to provide the catalyst with 4 grams/liter of elemental gold, and sodium hydroxide such that the Na/Cl mole ratio was about 1.8:1, to fix the gold on the support as auric hydroxide. The catalyst was then water washed until chloride free (about 5 hours) and dried at 150° C. for one hour in nitrogen flow. The palladium and auric hydroxides were then reduced to the metals by contacting the catalyst with ethylene (5% in nitrogen) in the vapor phase at 150° C. for 5 hours. Finally the catalyst was impregnated by incipient wetness with an aqueous solution of cupric acetate monohydrate in an amount sufficient to provide about 1.9 grams of elemental copper per liter of catalyst, and potassium acetate in an amount sufficient to provide 40 grams of potassium acetate per liter of catalyst, and dried in a fluid bed drier at 100–150° C. for one hour.

The catalyst prepared as described in the example was tested for its activity in the production of vinyl acetate by reaction of ethylene, oxygen and acetic acid. To accomplish this, about 60 ml of the catalyst prepared as described were placed in a stainless steel wire basket with the temperature capable of being measured by a thermocouple at both the top and bottom of the basket. The basket was placed in a Berty continuously stirred tank reactor of the recirculating type and was maintained at a temperature which provided about 45% oxygen conversion with an electric heating mantle. A gas mixture of about 130 l/hr (measured at N.T.P.) of ethylene, about 26 l/hr of oxygen, about 128 l/hr of nitrogen, about 131 g/hr of acetic acid, and about 2 mg/hr of potassium acetate, was caused to travel under pressure at about 12 atmospheres through the basket. The reaction was terminated after about 18 hours. Analysis of the products was accomplished by on-line gas chromatographic analysis combined with off-line liquid product analysis by condensing the product stream at about 10° C. to obtain optimum analysis of the end products. Such analysis indicated a $CO_2$ selectivity of 7.35%, a heavy ends selectivity of 0.98%, and a relative activity of the reaction expressed as an activity factor of 1.70 which is computer calculated in the following way: The computer program uses a series of equations that correlates the activity factor with the catalyst temperature (during the reaction), oxygen conversion, and a series of kinetic parameters for the reactions that take place during vinyl acetate synthesis. More generally, the activity factor is inversely related to the temperature required to achieve constant oxygen conversion.

The $CO_2$ selectivity of 7.35% obtained with this example is substantially lower than that usually obtained with similarly prepared 7 mm palladium-gold catalysts not containing any cupric acetate. It was found that a 7 mim Pd/Au catalyst devoid of cupric acetate and prepared as described for example 1 exhibited a $CO_2$ selectivity of about 9.3% and an activity of about 2.2.

What is claimed is:

1. A method for the production of vinyly acetate by reaction of ethylene, oxygen, and acetic acid comprising impregnating a porous support containing deposits of catalytically effective amounts of mectallic palladium and gold, with a solution of cupric acetate, wherein the porous support is prepared by steps comprising impregnating a porous support with an aqueous solution of a water-soluble palladium salt, fig said palladium as a water-insoluble compound by reaction with an appropriate alkaline compound, subsequently impregnating the catalyst with a solution of a water-soluble gold salt, fixing the gold in the solution present in the latter impregnation by relating the dissolved water-soluble salt in such solution with au appropriate alkaline compound to precipitate a water-insoluble gold compound, and reducing to their metallic state the water-insoluble compounds of palladium and gold present in the catalyst.

2. A method for the production of vinyl acetate by reaction of ethylene oxygen, and acetic acid comprising impregnating a porous support containing deposits of catalytically effective amounts of metallic palladium and gold, with a solution of cupric acetate, wherein the porous support is prepared by steps comprising impregnating the, support with a solution of an amount of water-soluble palladium sat containing all of the elemental palladium desired on the finished catalyst and an amount of water-soluble, gold salt containing only part of the elemental gold desired on the finished catalyst, fixing the palladium and gold in the latter solution as water-insoluble compounds by rotating and/or tumbling the impregnated support while it is immersed in a solution of an appropriate alkaline compound, reducing the fixed palladium and gold to their metallic state, impregnating the catalyst wit another solution of an amount of water soluble gold salt such that the total amount of elemental gold in the catalyst is equal to that desired in the finished catalyst, said latter solution also containing an amount of appropriate alkaline compound sufficient to fix the added gold as a water-insoluble compound, and reducing the fixed added gold to its metallic state.

3. The method of claim 1 or 2 wherein said impregnation is such that the cupric acetate deposited on the impregnated catalyst contains about 0.3 to about 5.0 grams of elemental copper per liter of catalyst.

4. The method of claim 1 or 2 wherein said cupric acetate contains about 0.5 to about 3.0 grams of elemental copper per liter of catalyst.

5. The method of claim 1 or 2 wherein said porous support contains about 1 to about 10 grams of palladium, and about 0.5 to about 10 grams of gold per liter of catalyst, with the amount of gold being from about 10 to about 125 wt. % based on the weight of palladium.

6. The method of claim 1 or 2 wherein said solution of cupric acetate also contains a dissolved alkali metal acetate.

7. The method of claim 1 or 2 wherein said alkali metal acetate is potassium acetate which is deposited on the catalyst in an amount of about 10 to about 70 grams/liter of catalyst.

\* \* \* \* \*

UNITED STATES PATENT AND TRADEMARK OFFICE
CERTIFICATE OF CORRECTION

PATENT NO.    : 5,948,724
DATED         : September 7, 1999
INVENTOR(S)   : Nicolau et al.

It is certified that error appears in the above-identified patent and that said Letters Patent is hereby corrected as shown below:

<u>Title page,</u>
Item [22], Filing Date: delete "29" between "October" and ",1997" and replace with -- 28 --.

<u>Column 6,</u>
Line 29, delete "vinyly" between "of" and "acetate" and replace with -- vinyl --.
Line 32, delete "mectallic" between "of" and "palladium" and replace with -- metallic --.
Line 36, delete "fig" and replace with -- fixing --.
Line 40, delete "relating" between "by" and "the" and replace with -- reacting --.
Line 41, delete "au" and replace with -- an --.
Line 52, delete "sat" after "palladium" and replace with -- salt --.
Line 61, delete "wit" between "catalyst" and "another" and replace with -- with --.

Signed and Sealed this

Twenty-sixth Day of November, 2002

Attest:

Attesting Officer

JAMES E. ROGAN
Director of the United States Patent and Trademark Office